United States Patent [19]

DiLeo et al.

[11] Patent Number: 4,902,846

[45] Date of Patent: Feb. 20, 1990

[54] SYNLUBE PROCESS

[75] Inventors: Thomas J. DiLeo; Matthew J. Lynch; Marshall B. Nelson; Ronny W. Lin, all of Baton Rouge, La.

[73] Assignee: Ethyl Corporation, Richmond, Va.

[21] Appl. No.: 305,716

[22] Filed: Feb. 2, 1989

Related U.S. Application Data

[63] Continuation-in-part of Ser. No. 225,872, Jul. 29, 1988, abandoned.

[51] Int. Cl.$^4$ ............................. C07C 2/04; C07C 2/02
[52] U.S. Cl. ..................................... 585/525; 585/510
[58] Field of Search ................................. 585/525, 510

[56] References Cited

U.S. PATENT DOCUMENTS

| | | | |
|---|---|---|---|
| 2,657,245 | 10/1953 | Davidson | 585/510 |
| 3,382,291 | 5/1968 | Brennan | 585/525 |
| 4,213,001 | 7/1980 | Madgavkar et al. | 585/510 |
| 4,239,930 | 12/1980 | Allphin et al. | 585/525 |
| 4,300,006 | 11/1981 | Nelson | 585/525 |
| 4,319,064 | 3/1982 | Heckelsberg et al. | 585/510 |
| 4,587,368 | 5/1986 | Pratt | 585/525 |

Primary Examiner—Patrick P. Garvin
Assistant Examiner—E. D. Irzinski
Attorney, Agent, or Firm—J. D. Odenweller

[57] ABSTRACT

$C_{8-14}$ α-olefins are oligomerized to a oligomer mixture containing a high content of tetramer by feeding the α-olefin to a reaction vessel at a controlled rate over an extended period and in the presence of $BF_3$ and a promoter such as an alcohol.

13 Claims, No Drawings

SYNLUBE PROCESS

CROSS-REFERENCE TO RELATED APPLICATION

This application is a Continuation-in-Part of application Ser. No. 225,872 filed July 29, 1988and now abandoned.

BACKGROUND

Alpha-olefin oligomers and their use as hydraulic fluids and synthetic lubricants (synlubes) are well known. U.S. Pat. No. 2,937,129 reports the oligomerization of $C_{5-14}$ α-olefins using a dialkyl peroxide catalyst to make a synlube. U.S. Pat. No. 3,113,167 describes an α-olefin oligomer process using a titanium halide and an aluminum compound.

The preferred catalysts for making α-olefin oligomers are Friedel Crafts metal halides such as $BF_3$, U.S. Pat. No. 3,149,178. Optimum properties are obtained starting with 1-decene although mixtures of α-olefins have been used, U.S. Pat. No. 3,330,883.

The preferred Friedel Crafts catalyst is $BF_3$. Pure $BF_3$ is not an effective oligomerization catalyst. A small amount of polar compound is necessary as a promoter. U.S. Pat. No. 3,382,291 describes the use of alcohol promoters such as decanol. Other reported promoters are modenite (hydrogen form), water, phosphoric acid, fatty acids (e.g. valeric acid), ketones, organic esters, ethers, polyhydric alcohols, silica gel and the like.

Synlubes are generally classified by their viscosity at 100° C. The viscosities most often referred to are 4, 6 and 8 centistokes (cs). Oligomers made from α-olefins are mixtures of dimer, trimer, tetramer, pentamer and small amounts of higher oligomers. Dimers are too volatile for most uses and are usually removed by distillation together with any unreacted monomer. In the case of 1-decene, 4 cs fluids are mainly trimer with a small amount of tetramer. The 4 cs synlubes can be merely distilled from the oligomer mixture leaving a more viscous residue that can be used to make 6 and 8 cs fluids. If demand for 6 and 8 cs fluids becomes large, the above procedure can be impractical because it could leave a manufacturer with an excess amount of trimer. Therefore a need exists for a procedure for making 6 and 8 cs fluids directly without the need for distilling out excessive amounts of trimer.

Pratt, U.S. Pat. No. 4,587,368, describes a process that results in increased tetramers and pentamers. Pratt achieves this in a 2-stage process by first conducting a conventional batch oligomerization procedure using a $BF_3$-propanol-hexanol catalyst until the mixture contains only 3-5 weight percent monomer. Then, in the second stage, additional α-olefin is added over an extended period to consume part of the trimer formed in the first stage thus increasing the amount of tetramer.

SUMMARY OF THE INVENTION

It has now been discovered that oligomers having increased amounts of tetramer and higher components can be made in a single-stage procedure by merely feeding an α-olefin over an extended period to a reaction vessel in the presence of $BF_3$ and a promoter.

DESCRIPTION OF THE PREFERRED EMBODIMENT

A preferred embodiment of the invention is a one-step batch process for making an α-olefin oligomer having increased tetramer content, said process comprising:

(A) placing an initial amount of 0–1.0 mole parts of a $C_{8-14}$ α-olefin in a reaction vessel and (B) feeding at least 0.5 mole parts of said $C_{8-14}$ α-olefin to said reaction vessel at a controlled rate over an extended time period in the presence of $BF_3$ and a promoter while maintaining the reaction temperature at about 20°–50° C., said feeding being commenced before said initial amount of $C_{8-14}$ α-olefin, if any, has oligomerized to any substantial extent.

The present process results in an α-olefin oligomer having an increased tetramer content compared to the tetramer content one would obtain with the same α-olefin, $BF_3$ catalyst, promoter and reaction temperature but conducted by charging all of the α-olefin prior to or at the start of the oligomerization.

Alpha-olefins useful in the process are those containing about 8–12 carbon atoms such as 1-octene, 1-decene and 1-dodecene including mixtures of such olefins. The olefins are mainly linear terminal olefins. The most preferred olefin is 1-decene.

The process is conducted in the presence of $BF_3$ and a promoter. In one mode, $BF_3$ is merely bubbled through the reaction mixture during the oligomerization. In a preferred mode, the process is conducted under $BF_3$ pressure. A useful pressure is about 1–100 psig, preferably 5–50 psig and more preferably about 10–20 psig.

The $BF_3$ pressure is applied at the start of or just prior to the additional α-olefin feed. Operating in this manner makes it unnecessary to add $BF_3$ to the reaction mixture through any other source such as by pre-saturating the α-olefin or a portion of the α-olefin with $BF_3$. Hence it is highly preferred to use a substantially $BF_3$-free α-olefin feed.

Any of the known promoters for $BF_3$ can be used such as water, alcohol (e.g. methanol, ethanol, n-propanol, isopropanol, n-butanol, isobutanol, n-hexanol, 2-ethyl hexanol, n-decanol, n-dodecanol and the like including mixtures thereof), fatty acids (e.g. valeric, caproic and the like), organic esters (e.g. butyl acetate, methyl valerate, ethyl octanoate, and the like), ketones (e.g. methyl ethyl ketone, methyl isobutyl ketone, and the like), ethers (e.g. dibutyl ether, tetrahydrofuran, dioxane and the like), alkoxylated alcohols (e.g. 2-ethoxyethanol, and the like), polhydric alcohols (e.g. glycol, glycerol and the like), inorganic acids (e.g. phosphoric and the like), silica, zeolites and the like.

The more preferred promoters are the alcohols, especially n-butanol.

The amount of promoter should be an amount that causes the $BF_3$ to act as an oligomerization catalyst. This is referred to as a promoter amount. A useful range is about 0.1–2.0 weight percent of the -olefin. At the start of the process there is very little or none of the α-olefin in the reaction vessel. Because of this it is preferred to add the promoter to the reaction vessel over an extended period of time such that the concentration of the promoter in the liquid phase remains in the desired range. The promoter can be added in spaced increments or can be continuously fed over a prolonged period. This will generally be substantially the same as the extended period of α-olefin feed, although this is not essential. Preferably the prolonged period of promoter addition is at least one-half hour and more preferably an hour or longer. There is no critical upper limit to the promoter feed time. The length of the prolonged period of promoter feed depends upon the length of the extended period of α-olefin feed. A time range for feeding the promoter is 0.5 up to 24 hours. A preferred time range is 0.5 up to the α-olefin feed time and, more preferably, one hour up to the α-olefin feed time.

The promoter is preferably fed to the reaction mixture in a continuous manner throughout the promoter feed period. Optionally the promoter can be added in a series of incremental feeds. For example a portion of the promoter can be fed every 15 minutes or so to maintain the promoter concentration in the desired 0.1–2.0 weight percent range. If the promoter is miscible with the α-olefin it can be merely mixed or dissolved in the α-olefin which is fed at a controlled rate over an extended period.

At the start of the process there need not be any α-olefin in the reaction vessel. This is why the initial amount is defined as 0–1.0 moles. Preferably a portion of the α-olefin is initially charged at the start of the process. This enables the reaction vessel agitator to engage a liquid phase. Hence in a still more preferred mode of operation, an initial charge of about 0.1–1.0 mole parts of α-olefin are placed in the reaction vessel at the start.

The process is carried out by injecting $BF_3$ and promoter into the reaction vessel and gradually feeding α-olefin. If an initial charge of α-olefin is in the reactor, the controlled feed of the α-olefin is commenced before the initial α-olefin charge has oligomerized to any substantial extent. This means at least 75 weight percent and more preferably at least 90 weight percent of any initial α-olefin charge is still monomer when the controlled feed of the α-olefin over an extended period is commenced.

The amount of α-olefin fed to the reaction vessel at a controlled rate over an extended period is at least 0.5 mole parts, preferably about 0.5–100 mole parts and more preferably about 0.5–10 mole parts by weight. This has little significance if the initial α-olefin charge is zero, but if there is any initial charge, it establishes a weight ratio between initial α-olefin charge and the amount of α-olefin fed over an extended period. Broadly this is 0–1.0:0.5–100. More preferably this weight ratio is 0.1–1.0:0.5–100 and still more preferably 0.25–0.8:0.5–10.0.

The time of addition of the α-olefin at a controlled rate is an extended period. This means it takes place over a period of time rather than all at once. The extended period should be at least one-half hour and preferably at least one hour. There is no critical upper limit to the α-olefin extended feed time. As a practical matter there is little advantage in an extended feed time in excess of 24 hours. A more preferred extended α-olefin feed period is 0.5–12 hours and still more preferably 1.0–8 hours.

The α-olefin is fed at a controlled rate. This means the process includes some means to control the rate of α-olefin feed such that it is not all charged to the reaction vessel prior to the start of the reaction. The feed control means can be a valve to adjust α-olefin feed from a head tank or can be a conventional flow meter. The α-olefin feed is preferably continuous over the entire extended feed period but can be conducted in a series of incremental feed periods. For example an increment of the α-olefin can be added every 15 minutes until the total α-olefin has been added.

The preferred reaction temperature is about 20°–50° C. and more preferably about 25°–40° C. Superior results have been achieved at about 30° C. Lower temperatures will increase the amount of higher oligomers but at the cost of a slower reaction rate. High temperatures give a fast reaction rate but increased yield of dimer. The following examples show a conventional process for making α-olefin oligomers compared to the present process for making such oligomers.

EXAMPLE 1

This example shows a comparative procedure for making an α-olefin oligomer which uses promoter feed over a prolonged period but charges all of the α-olefin at the start.

In a reaction vessel was placed 2000 g of 1-decene. The vessel was sealed and pressurized to 20 psig with $BF_3$. While stirring, 12 g of n-butanol (0.6 weight percent of 1-decene) was continuously fed to the reaction mixture over a one-hour period while stirring at 30° C. Stirring was continued for 1.5 hours at which time the mixture was washed with 30 weight percent aqueous caustic to remove $BF_3$ and n-butanol. The product was then analyzed by gas chromatograph (GC) which gave the results shown in Table I.

EXAMPLE 2

This example shows how the present process can be conducted.

In a reaction vessel was placed 1000 g of 1-decene. The vessel was pressurized to 20 psig with $BF_3$. While stirring at 30° C., 800 g of additional 1-decene containing 0.6 weight percent n-butanol was continuously fed to the reactor over a 2.6 hour period. Six grams of n-butanol was continuously fed to the reactor over a one-hour period. After completion of the 1-decene programmed feed, stirring was continued at 30° C. for 15 minutes. The reaction mixture was then washed with aqueous caustic to remove $BF_3$ and n-butanol and analyzed by GC. Results are shown in Table I.

These results show that the present one-step programmed feed process results in a sharp increase in tetramer and higher oligomers. Decene oligomers containing at least 40 weight percent tetramer and having a tetramer/trimer ratio of at least 1.5 are readily obtained. After distillation to remove the monomer and dimer and optionally some of the trimer, the product can be catalytically hydrogenated to obtain a 6 or 8 cs synlube.

We claim:
1. A one-step batch process for making an α-olefin oligomer, said process comprising:
   (A) placing an initial amount of 0–1.0 mole parts of a $C_{8-14}$ α-olefin which is substantially free of promoted $BF_3$ catalyst in a reaction vessel and
   (B) co-feeding at least 0.5 additional mole parts of said $C_{8-14}$ α-olefin and a $BF_3$ promoter to said reaction vessel over a period of at least one-half hour and under $BF_3$ pressure while maintaining the reaction temperature at about 20°–50° C., said co-feeding being commenced at a time when said initial amount of $C_{8-14}$ α-olefin, if any, is still at least 75 weight percent monomer.

2. A process of claim 1 wherein said promoter is an alcohol.

3. A process of claim 2 wherein said alcohol is n-butanol and said process is conducted under a $BF_3$ pressure of 1–100 psig.

4. A process of claim 3 wherein said α-olefin is 1-decene.

5. A process of claim 4 wherein said reaction temperature is 25°–40° C.

6. A process of claim 3 wherein said alcohol promoter is added to said reaction vessel over a period of at least one-half hour such that the concentration of alcohol promoter in the liquid phase remains in a range of about 0.1–2.0 weight 7. A process of claim 6 wherein said α-olefin is 1-decene.

8. A process of claim 7 wherein said additional $C_{8-14}$ α-olefin is added to said reaction vessel over a period of at least one hour.

9. A process of claim 8 wherein said alcohol promoter is added to said reaction vessel over a period of at least one hour.

10. A batch process for making a 1-decene oligomer containing at least 40 weight percent tetramer, said process comprising:
  (A) initially placing 0.1–1.0 mole parts of 1-decene which is substantially free of promoted $BF_3$ catalyst in a reaction vessel, and
  (B) feeding (i) at least an additional 0.5 moles of 1-decene and (ii) a promoter amount of an alcohol to said reaction vessel over a period of at least 1 hour at a reaction temperature of about 25°–40° C. while maintaining said reaction vessel under $BF_3$ pressure.

11. A process of claim 10 wherein said alcohol is n-butanol.

12. A process of claim 11 wherein said temperature is about 25°–35° C.

13. A process of claim 10 wherein said reaction is continued after completion of said 1-decene and alcohol feed until the combined monomer and dimer content of the reaction mixture is below about 5 weight percent.

* * * * *